(12) United States Patent
Colleran

(10) Patent No.: US 7,569,061 B2
(45) Date of Patent: Aug. 4, 2009

(54) OFF-AXIS ANCHOR GUIDANCE SYSTEM

(75) Inventor: Dennis Colleran, Frisco, MA (US)

(73) Assignee: Innovative Spinal Technologies, Inc., Plano, TX (US)

( * ) Notice: Subject to any disclaimer, the term of this patent is extended or adjusted under 35 U.S.C. 154(b) by 0 days.

(21) Appl. No.: 10/991,845

(22) Filed: Nov. 18, 2004

(65) Prior Publication Data

US 2006/0106394 A1    May 18, 2006

Related U.S. Application Data

(63) Continuation-in-part of application No. 10/990,272, filed on Nov. 16, 2004.

(51) Int. Cl.
*A61F 5/00* (2006.01)
*A61B 17/56* (2006.01)
*A61B 17/58* (2006.01)

(52) U.S. Cl. ............... 606/104; 606/279; 606/86 A; 606/86

(58) Field of Classification Search ............ 606/72–73, 606/86, 99, 104, 86 A, 914, 916, 246, 279
See application file for complete search history.

(56) References Cited

U.S. PATENT DOCUMENTS

| | | | |
|---|---|---|---|
| 1,522,927 A | 1/1925 | Wickstrom et al. | |
| 1,712,196 A | 5/1929 | Burger et al. | |
| 1,737,488 A | 11/1929 | Zohlen | |
| 2,248,054 A * | 7/1941 | Becker | 81/457 |
| 2,302,691 A | 11/1942 | Green | |
| 2,329,398 A * | 9/1943 | Duffy | 606/104 |
| 2,952,285 A | 9/1960 | Roosli | |
| 3,989,284 A | 11/1976 | Blose | |
| 4,140,111 A | 2/1979 | Morrill | |
| 4,233,974 A | 11/1980 | Desecki et al. | |

(Continued)

FOREIGN PATENT DOCUMENTS

DE          9112466 U1    1/1992

(Continued)

OTHER PUBLICATIONS

European Patent Office; International Search Report of International patent application No. PCT/US2005/041028; Mar. 3, 2006.

*Primary Examiner*—Eduardo C Robert
*Assistant Examiner*—Mary Hoffman
(74) *Attorney, Agent, or Firm*—Eckert Seamans Cherin & Mellott, LLC; Carol A. Marmo, Esq.

(57) ABSTRACT

Disclosed is a guided bone anchoring device comprising a head, a shank and a passage for receiving a guide wire, the passage having a longitudinal center axis which is not concentric to the longitudinal center axis of the shank. Also disclosed is a system for guiding bone anchors, the system comprising: a guide wire, an anchor comprised of a shank wherein the shank has an offset bore at the distal end which is adapted to allow the guide wire to slide through the bore, a dilator having a longitudinal slot wherein the longitudinal slot allows the guide wire to extend through the longitudinal slot when the anchor is positioned within the dilator, and a driving device which is adapted to engage the proximal end of the anchor.

4 Claims, 8 Drawing Sheets

U.S. PATENT DOCUMENTS

| | | | |
|---|---|---|---|
| 4,511,356 A | 4/1985 | Froning et al. | |
| 4,792,339 A | 12/1988 | Tepi | |
| 4,827,918 A | 5/1989 | Olerud | |
| 4,917,409 A | 4/1990 | ReeveS | |
| 5,047,029 A | 9/1991 | Aebi et al. | |
| 5,098,435 A * | 3/1992 | Stednitz et al. | 606/73 |
| 5,116,337 A * | 5/1992 | Johnson | 606/73 |
| 5,120,171 A | 6/1992 | Lasner | |
| 5,171,279 A | 12/1992 | Mathews | |
| 5,176,680 A | 1/1993 | Vignaud et al. | |
| 5,196,014 A | 3/1993 | Lin | |
| 5,196,015 A | 3/1993 | Neubardt | |
| 5,242,443 A | 9/1993 | Kambin | |
| 5,258,016 A * | 11/1993 | DiPoto et al. | 606/232 |
| 5,261,913 A | 11/1993 | Marnay | |
| 5,282,863 A | 2/1994 | Burton | |
| 5,312,438 A * | 5/1994 | Johnson | 606/232 |
| 5,334,204 A * | 8/1994 | Clewett et al. | 606/73 |
| 5,357,983 A | 10/1994 | Mathews | |
| 5,458,608 A | 10/1995 | Wortrich | |
| 5,472,426 A | 12/1995 | Bonati | |
| 5,480,440 A | 1/1996 | Kambin | |
| 5,496,322 A | 3/1996 | Mathews | |
| 5,520,689 A | 5/1996 | Schlapfer et al. | |
| 5,526,812 A | 6/1996 | Dumoulin et al. | |
| 5,536,268 A | 7/1996 | Griss | |
| 5,569,248 A | 10/1996 | Mathews | |
| 5,605,457 A | 2/1997 | Bailey et al. | |
| 5,605,458 A | 2/1997 | Bailey et al. | |
| 5,607,304 A | 3/1997 | Bailey et al. | |
| 5,628,740 A | 5/1997 | Mullane | |
| 5,643,260 A | 7/1997 | Doherty | |
| 5,645,549 A | 7/1997 | Boyd et al. | |
| 5,667,513 A | 9/1997 | Torrie et al. | |
| 5,716,355 A | 2/1998 | Jackson et al. | |
| 5,725,581 A * | 3/1998 | Branemark | 606/73 |
| 5,728,097 A | 3/1998 | Mathews | |
| 5,733,286 A | 3/1998 | Errico et al. | |
| 5,733,307 A * | 3/1998 | Dinsdale | 606/232 |
| 5,741,261 A | 4/1998 | Moskovitz et al. | |
| 5,741,268 A | 4/1998 | Schutz | |
| 5,769,852 A * | 6/1998 | Brånemark | 606/65 |
| 5,785,707 A | 7/1998 | Boyd et al. | |
| 5,792,044 A | 8/1998 | Foley et al. | |
| 5,885,292 A | 3/1999 | Moskovitz et al. | |
| 5,891,147 A | 4/1999 | Moskovitz et al. | |
| 5,902,231 A | 5/1999 | Foley et al. | |
| 5,910,142 A | 6/1999 | Tatar | |
| 5,954,635 A | 9/1999 | Foley et al. | |
| 5,954,671 A | 9/1999 | O'Neill | |
| 5,984,923 A | 11/1999 | Breard | |
| 6,007,487 A | 12/1999 | Foley et al. | |
| 6,074,391 A | 6/2000 | Metz-Stavenhagen et al. | |
| 6,077,262 A | 6/2000 | Schlapfer et al. | |
| 6,090,113 A | 7/2000 | Le couedic | |
| 6,096,044 A | 8/2000 | Boyd et al. | |
| 6,113,604 A | 9/2000 | Whittaker et al. | |
| 6,132,433 A | 10/2000 | Whelan | |
| 6,132,443 A | 10/2000 | Whelan et al. | |
| 6,152,871 A | 11/2000 | Foley et al. | |
| 6,162,170 A | 12/2000 | Foley et al. | |
| 6,176,823 B1 | 1/2001 | Foley et al. | |
| 6,206,822 B1 | 3/2001 | Foley et al. | |
| 6,210,376 B1 * | 4/2001 | Grayson | 604/264 |
| 6,217,509 B1 | 4/2001 | Foley et al. | |
| 6,235,028 B1 | 5/2001 | Brumfield et al. | |
| 6,254,146 B1 | 7/2001 | Church | |
| 6,264,658 B1 | 7/2001 | Lee et al. | |
| 6,287,313 B1 | 9/2001 | Sasso | |
| 6,296,642 B1 | 10/2001 | Morrison et al. | |
| 6,302,888 B1 | 10/2001 | Mellinger et al. | |
| 6,340,363 B1 | 1/2002 | Bolger et al. | |
| 6,395,007 B1 | 5/2002 | Bhatnagar et al. | |
| 6,402,757 B1 * | 6/2002 | Moore et al. | 606/80 |
| 6,425,859 B1 | 7/2002 | Foley et al. | |
| 6,485,491 B1 | 11/2002 | Farris et al. | |
| 6,520,907 B1 | 2/2003 | Foley et al. | |
| 6,530,929 B1 | 3/2003 | Justis et al. | |
| 6,546,277 B1 | 4/2003 | Franck et al. | |
| 6,551,316 B1 | 4/2003 | Rinner et al. | |
| 6,551,318 B1 | 4/2003 | Stahurski | |
| 6,562,046 B2 | 5/2003 | Sasso | |
| 6,575,899 B1 | 6/2003 | Foley et al. | |
| 6,626,904 B1 | 9/2003 | Jammet et al. | |
| 6,648,893 B2 | 11/2003 | Dudasik | |
| 6,679,833 B2 | 1/2004 | Smith | |
| 6,706,044 B2 | 3/2004 | Kuslich et al. | |
| 6,726,689 B2 | 4/2004 | Jackson | |
| 6,726,692 B2 | 4/2004 | Bette | |
| 6,755,829 B1 | 6/2004 | Bono et al. | |
| 6,770,075 B2 | 8/2004 | Howland | |
| 6,786,907 B2 | 9/2004 | Lange | |
| 6,793,656 B1 | 9/2004 | Mathews | |
| 6,802,844 B2 | 10/2004 | Ferree | |
| 6,814,734 B2 | 11/2004 | Chappuis et al. | |
| 6,818,010 B2 * | 11/2004 | Eichhorn et al. | 606/232 |
| 6,827,722 B1 | 12/2004 | Schoenefeld | |
| 6,837,889 B2 | 1/2005 | Shluzas | |
| 6,837,891 B2 | 1/2005 | Davison et al. | |
| 6,843,790 B2 | 1/2005 | Ferree | |
| 6,849,064 B2 | 2/2005 | Hamada | |
| 6,890,333 B2 | 5/2005 | von Hoffmann et al. | |
| 6,899,714 B2 | 5/2005 | Vaughan | |
| 6,905,501 B2 | 6/2005 | Nakamura et al. | |
| 6,916,330 B2 | 7/2005 | Simonson et al. | |
| 6,926,728 B2 | 8/2005 | Zucherman et al. | |
| 6,949,100 B1 | 9/2005 | Venturini | |
| 6,953,462 B2 | 10/2005 | Lieberman | |
| 6,979,334 B2 | 12/2005 | Dalton | |
| 7,066,937 B2 | 6/2006 | Shluzas | |
| 7,083,621 B2 | 8/2006 | Shaolian et al. | |
| 7,144,396 B2 | 12/2006 | Shluzas | |
| 7,179,261 B2 | 2/2007 | Sicvol et al. | |
| 2001/0034526 A1 | 10/2001 | Kuslich et al. | |
| 2002/0058942 A1 | 5/2002 | Biedermann et al. | |
| 2002/0095153 A1 | 7/2002 | Jones et al. | |
| 2002/0123754 A1 | 9/2002 | Holmes et al. | |
| 2002/0138077 A1 | 9/2002 | Ferree | |
| 2003/0208203 A1 | 11/2003 | Lim et al. | |
| 2004/0039384 A1 | 2/2004 | Boehm et al. | |
| 2004/0049196 A1 | 3/2004 | Jackson | |
| 2004/0106997 A1 | 6/2004 | Lieberson | |
| 2004/0133203 A1 | 7/2004 | Young et al. | |
| 2004/0138662 A1 | 7/2004 | Landry et al. | |
| 2004/0143265 A1 | 7/2004 | Landry et al. | |
| 2004/0147936 A1 | 7/2004 | Rosenberg et al. | |
| 2004/0172022 A1 | 9/2004 | Landry et al. | |
| 2004/0176766 A1 | 9/2004 | Shluzas | |
| 2004/0215190 A1 | 10/2004 | Nguyen et al. | |
| 2004/0267279 A1 | 12/2004 | Casutt et al. | |
| 2005/0033299 A1 | 2/2005 | Shluzas | |
| 2005/0033433 A1 | 2/2005 | Michelson | |
| 2005/0065517 A1 * | 3/2005 | Chin | 606/61 |
| 2005/0070917 A1 | 3/2005 | Justis | |
| 2005/0070918 A1 | 3/2005 | Zwirnmann et al. | |
| 2005/0075540 A1 | 4/2005 | Shluzas et al. | |
| 2005/0075644 A1 | 4/2005 | DiPoto et al. | |
| 2005/0075647 A1 | 4/2005 | Walters et al. | |
| 2005/0080418 A1 | 4/2005 | Simonson et al. | |
| 2005/0080443 A1 | 4/2005 | Fallin et al. | |
| 2005/0085813 A1 | 4/2005 | Spitler et al. | |
| 2005/0090822 A1 | 4/2005 | DiPoto | |
| 2005/0090826 A1 | 4/2005 | Keller | |
| 2005/0090852 A1 | 4/2005 | Layne et al. | |

| | | | |
|---|---|---|---|
| 2005/0090899 A1 | 4/2005 | DiPoto | |
| 2005/0096652 A1 | 5/2005 | Burton | |
| 2005/0101961 A1 | 5/2005 | Huebner et al. | |
| 2005/0107801 A1 | 5/2005 | Davies et al. | |
| 2005/0119685 A1 | 6/2005 | Smith | |
| 2005/0131408 A1 | 6/2005 | Sicvol et al. | |
| 2005/0131421 A1 | 6/2005 | Anderson et al. | |
| 2005/0131422 A1 | 6/2005 | Anderson et al. | |
| 2005/0137595 A1 | 6/2005 | Hoffmann et al. | |
| 2005/0149030 A1 | 7/2005 | Serhan et al. | |
| 2005/0149031 A1 | 7/2005 | Ciccone et al. | |
| 2005/0149035 A1 | 7/2005 | Pimenta et al. | |
| 2005/0171551 A1 | 8/2005 | Sukovich et al. | |
| 2005/0177165 A1 | 8/2005 | Zang et al. | |
| 2005/0177166 A1 | 8/2005 | Timm et al. | |
| 2005/0177167 A1 | 8/2005 | Muckter | |
| 2005/0273101 A1 | 12/2005 | Schumacher | |
| 2005/0277919 A1 | 12/2005 | Slivka et al. | |
| 2005/0283244 A1 | 12/2005 | Gordon et al. | |
| 2006/0036244 A1 * | 2/2006 | Spitler et al. | 606/61 |
| 2006/0149252 A1 | 7/2006 | Markworth et al. | |

FOREIGN PATENT DOCUMENTS

| | | | |
|---|---|---|---|
| DE | 9402695 U1 | 5/1994 | |
| DE | 29903342 U1 | 7/1999 | |
| DE | 29810798 U1 | 12/1999 | |
| EP | 159007 A3 | 4/1986 | |
| EP | 1072228 A1 | 1/2001 | |
| EP | 1281365 A | 2/2003 | |
| EP | 1190678 A3 | 3/2003 | |
| EP | 1187568 B1 | 11/2005 | |
| EP | 1551320 B1 | 12/2005 | |
| FR | 2659546 A1 | 9/1991 | |
| WO | WO0128436 A1 | 4/2001 | |
| WO | WO03094741 A3 | 11/2003 | |
| WO | WO2004017847 A3 | 3/2004 | |
| WO | WO2004041100 A1 | 5/2004 | |
| WO | WO2004047650 A3 | 6/2004 | |
| WO | WO2004072496 A1 | 8/2004 | |
| WO | WO2004073534 A1 | 9/2004 | |
| WO | WO2004080318 A1 | 9/2004 | |
| WO | WO2004082464 A3 | 9/2004 | |
| WO | WO2005041799 A1 | 5/2005 | |
| WO | WO2005102191 A2 | 11/2005 | |
| WO | WO2005102194 A2 | 11/2005 | |
| WO | WO2005117727 A1 | 12/2005 | |
| WO | WO2005117731 A1 | 12/2005 | |
| WO | WO2005120401 A2 | 12/2005 | |
| WO | WO2005122926 A1 | 12/2005 | |
| WO | WO2005122930 A2 | 12/2005 | |
| WO | WO2006001993 A1 | 1/2006 | |
| WO | WO2006009794 A1 | 1/2006 | |

* cited by examiner

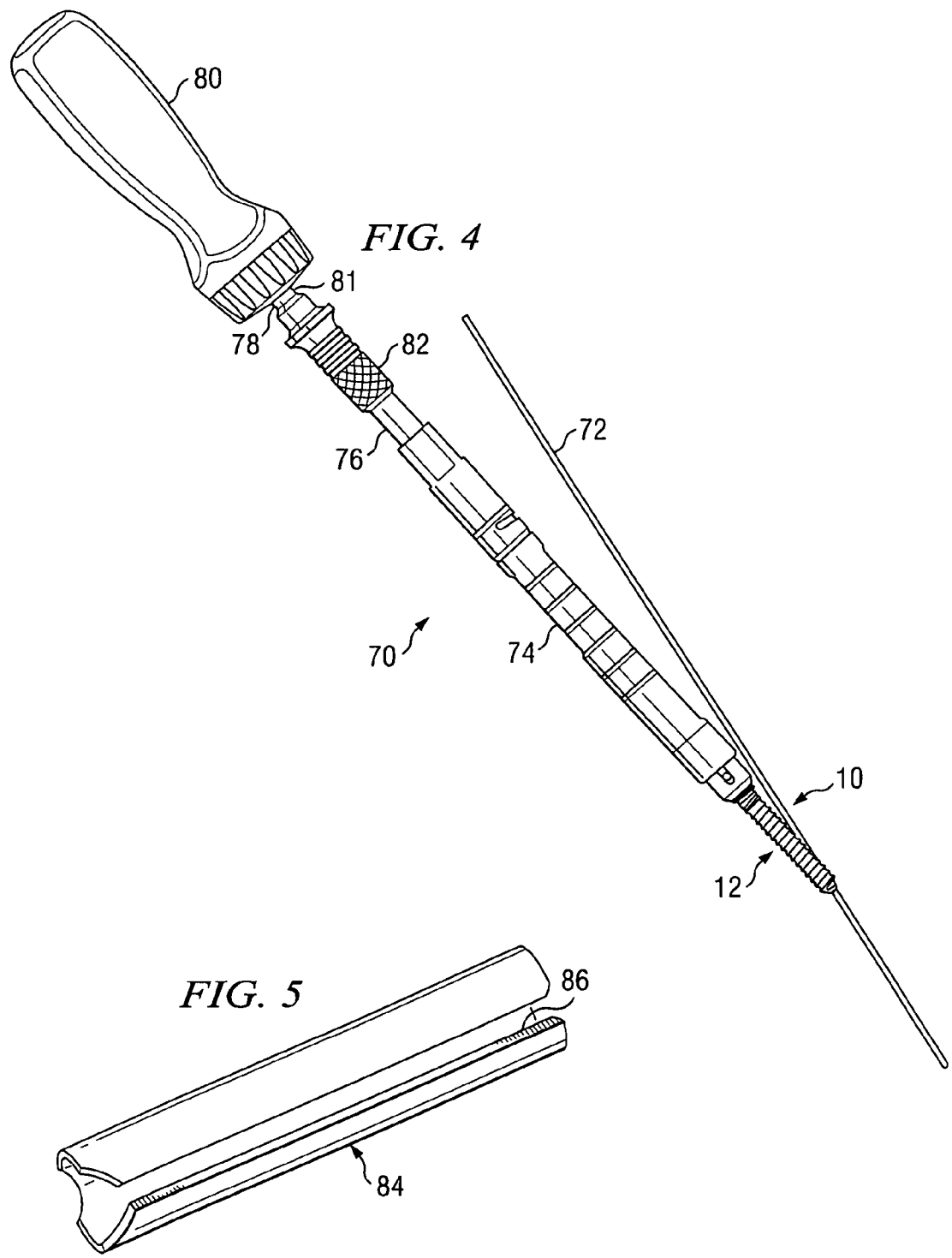

OFF-AXIS ANCHOR GUIDANCE SYSTEM

CROSS REFERENCE TO RELATED APPLICATIONS

This application is a continuation-in-part of patent application Ser. No. 10/990,272, entitled "An Implant Assembly And Method For Use In An Internal Structure Stabilization System" filed on Nov. 16, 2004, the disclosure of which is hereby incorporated by reference. This application is related to and claims priority to the following commonly-owned U.S. applications: U.S. application Ser. No. 10/989,715, entitled: An Extension for Use with Stabilization Systems for Internal Structures; U.S. application Ser. No. 10/989,782, entitled: Connector Transfer Tool for Internal Structure Stabilization Systems; and U.S. application Ser. No. 10/990,221, entitled: Internal Structure Stabilization System for Spanning Three or More Structures.

TECHNICAL FIELD

This application relates generally to the field of medical implant devices and more particularly to systems and methods for inserting and guiding bone anchoring devices.

BACKGROUND INFORMATION

Orthopedic injuries, deformities, and degenerative diseases often require intervention in the form of surgery for placing implants to stabilize an internal structure, promote healing, and relieve pain. In the area of spinal surgery, for example, a common procedure includes placement of pedicle screws that are joined by a connecting rod spanning between these screws. Once placed, the rod must be firmly secured to the bone securing elements to provide a stable construct which effectively immobilizes or creates a controlled dynamic motion to a corresponding portion of the spine.

One problem when connecting the rods to the pedicle screws is to position the rods in place as quickly as possible without doing more damage to the surrounding tissue and muscle of the patient. In order to reduce this damage, procedures have been developed that allow the physician to secure the pedicle screws in the bony portion of the spine and to then connect the rods or brace between the pedicle screws. Techniques have been developed to allow the surgeon to perform this procedure in a minimally invasive manner, utilizing a percutaneous method, inserting screws through small ports and avoiding an open approach.

In one such procedure, a surgeon identifies the desired vertebral level and pedicle positions via standard techniques. Once the target vertebrae are identified, a small incision is made through the patient's skin and a tracking needle (or other device) is inserted to pinpoint exactly where each pedicle screw is to be placed. A fluoroscope, or other x-ray technique, is used to properly position the tracking needle. Once the proper position is located, a guide wire is positioned with its distal end into the pedicle of vertebrae. The surgeon then slides a series of continuing larger sized dilators down the guide wire. The surgeon may also slide a hole tapping instrument over the guide wires. The hole tapping instrument may be used to tap a hole in the pedicle. After the hole is tapped, a cannulated pedicle screw and a modified screw driver may be inserted down the guide wire until the screw reaches the desired position. The position may be again checked with fluoroscopic techniques. For purposes of this application, a cannulated pedicle screw is defined as a pedicle screw that contains a cannulation centered and running entirely through its longitudinal axis.

After the position of the cannulated pedicle screw has been confirmed, the surgeon is ready to screw the cannulated pedicle screw into the vertebrae. After the cannulated pedicle screw has been inserted, this procedure may be repeated for each additional level. When one or more pedicle screws are in place, a brace or rod may be positioned by techniques known in the art. Under current practice, the physician then must work the brace, or other supporting device, so that each brace end is positioned properly with respect to the preplaced pedicle screws, and tighten the brace to each pedicle screw to complete assembly.

Once a patient recovers and become active, the brace may be subject to relatively large structural forces. These forces are applied to the shanks of the cannulated pedicle screws. Consequently, it is the shanks of the cannulated pedicle screws that resist the applied forces. To be more specific, it is the portion of the screw shank that is positioned within the pedicle of the vertebral body (approximately two-thirds of the length of the screw from the distal tip of the screw towards the proximal end of the screw) (the highest stress region is that region of the pedicle screw that is nearest the entry point of the pedicle, which tends to be about two thirds up from the distal tip of the pedicle screw).

When conventional pedicle screws are cannulated, a significant portion of their cross-sectional area is removed to create the cannulation. The cannulation, therefore, causes higher stress in the remaining portions of the shank which is subject to the applied forces. This causes a significant weakening of the screw. This weakening can cause failure of the pedicle screw which means that the patient would have to undergo additional surgery to have the pedicle screws replaced.

In order to minimize the reduction in strength of the screws, the cannulations are made as small as possible. This means that the guides wires must also be small, which may lead to advancement, kinking, breakage, or other problems during surgery. Inadvertent advancement of the guide wire is a critical concern to clinicians. If the guide wire becomes bent through off-angle manipulation by the surgeon, as the tap or screw is inserted, the tap or screw pushes the guide wire forward. This unwanted guide wire advancement could cause the guide wire to push forward through the anterior wall of the vertebral body, causing trauma to the patient.

What is needed, therefore, is a device and system which will allow for anchors to be guided and inserted into patients while maintaining the structural integrity and safety of the anchor and/or the guide wire.

SUMMARY

In response to these and other problems, in one embodiment, there is a guided bone anchoring device comprising: a head, a shank having a proximal end and a distal end, wherein the proximal end is coupled to the head, and an off-axis bore for accepting a guide.

Thus various aspects of this disclosure allows the shanks of wire guided anchors to resist larger forces than conventional cannulated screws because the offset bores do not cause a cannulation through the entire length of the anchor. Furthermore, the offset bore may be of a relatively larger diameter when compared to the conventional cannulation of conventional cannulated pedicle screws. The larger diameter bore results in a larger diameter guide wire which: increases the strength of the guide wire; reduces kinking; allows a surgeon to have tactile feedback regarding the placement and location of the guide wire; and allows the surgeon to maintain hold of the proximal end of the guide wire at all times throughout the procedure. Furthermore, the relative short length of the offset bore reduces the friction between the instruments and the guide wire, thereby reducing the likelihood of guide wire advancement.

These and other features and advantages will be more clearly understood from the following detailed description taken in conjunction with the accompanying drawings. It is important to note the drawings are not intended to represent the only aspect of the invention.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the invention is intended to encompass within its scope such processes, machines, manufacture, compositions of matter, means, methods, or steps.

BRIEF DESCRIPTION OF THE DRAWINGS

FIG. 4 illustrates a driving device coupled to an anchor which incorporates one or more aspects of the present invention.

FIG. 5 illustrates an isometric view of an illustrative embodiment of a dilator which incorporates one or more aspects of the present invention.

DETAILED DESCRIPTION

Figure 1:
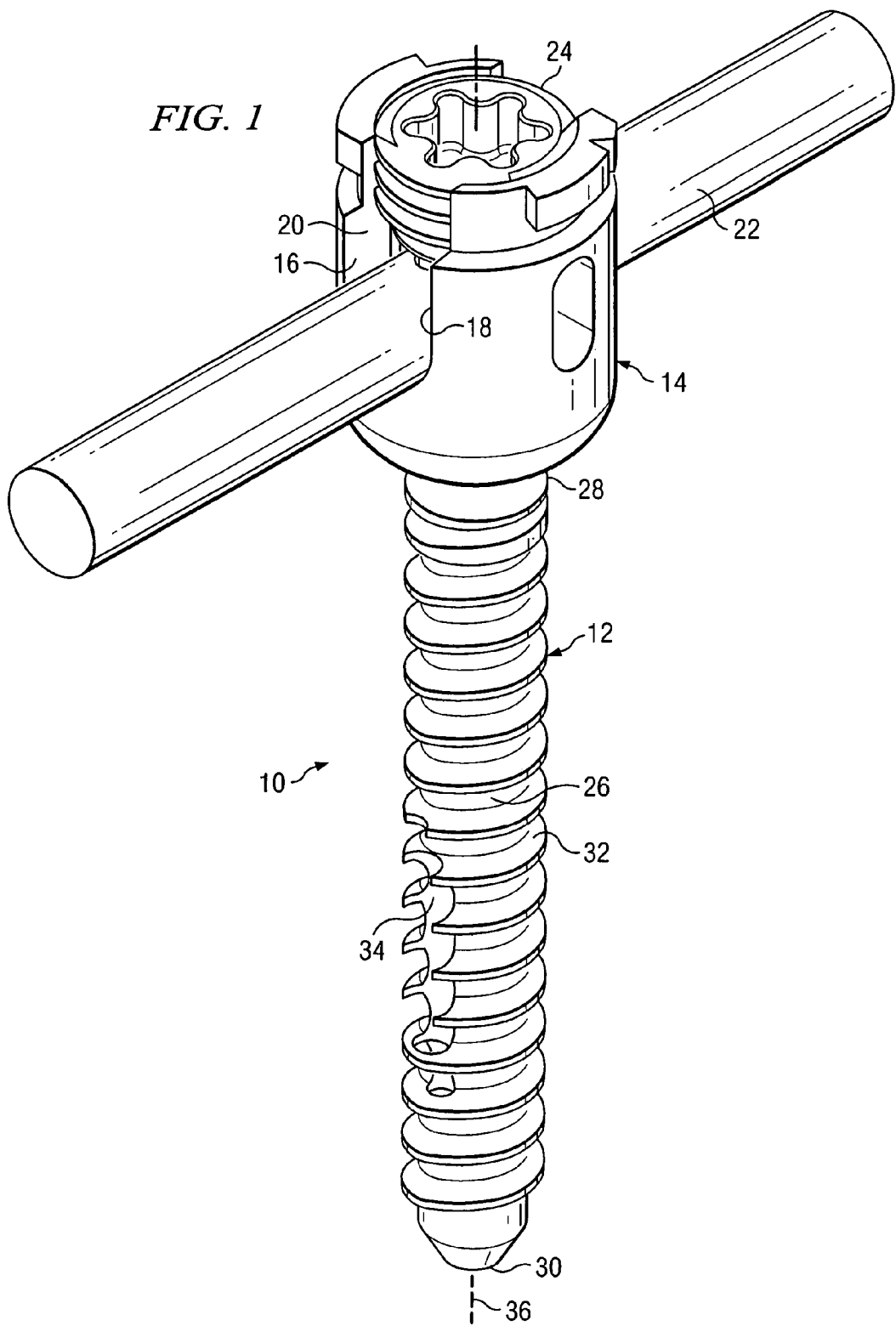
FIG. 1. illustrates an isometric view of an example medical implant device which incorporates one or more aspects of the present invention.

Turning now to FIG. 1, there is presented one illustrative embodiment of an anchoring system showing certain aspects of the present invention. As shown, a medical implant device 10 includes an anchor 12 which may be coupled to a rod receiving part 14. In some embodiments, the rod receiving part 14 may include noncontiguous walls 16 and 18 which form a channel 20 for receiving a rod 22. In some embodiments, there is a closure member 24 which engages the walls 16 and 18 and thus applies pressure to the rod 22 to effectively clamp about the rod 22, thereby positionally securing the rod 22 relative to the anchor 12. Such a closure member is more fully described in a co-pending and commonly assigned U.S. patent application Ser. No. 10/805,967 filed on Mar. 22, 2004 entitled "CLOSURE MEMBER FOR A MEDICAL IMPLANT DEVICE" (hereafter "the '967 patent application), which is hereby incorporated by reference.

In the illustrated embodiment, the anchor 12 has a shank 26 having a proximal end 28 and a distal end 30. In this example embodiment, the anchor 12 illustrates a screw and thus has a helical thread 32 positioned about the shank 26. It is important to note that although a screw is illustrated, the anchor 12 could be any suitable anchor having any suitable surface. For example, the anchor 12 could be a ring shank fastener, a barb, a nail, a brad or a trocar. Furthermore, the anchor 12 may also have an expandable diameter which allows the anchor to "lock" into the bone after placement.

Proximal to the distal end 30, there may be a bore 34 the center of which may be rotatedly offset from a longitudinal axis 36 of the shank 26. As illustrated, the bore 34 extends from the distal end 30 to the side of the shank 32.

Figure 2:
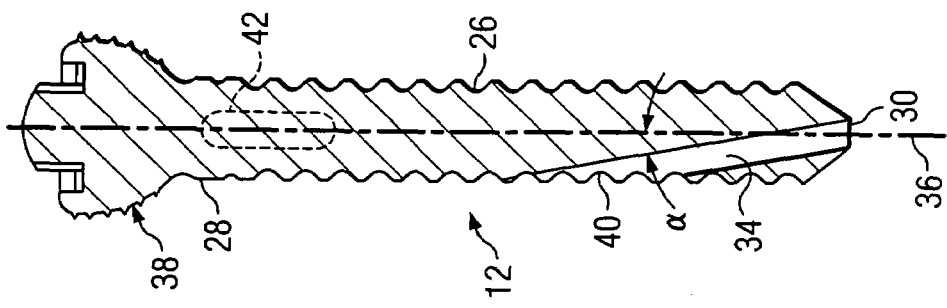
FIG. 2 illustrates a cross-section view of an illustrative embodiment of an anchoring device which incorporates one or more aspects of the present invention.

FIG. 2 illustrates a cross sectional view of one aspect of the anchor 12. In this view, it can be seen that the anchor 12 has a head 38 coupled to the proximal end 28 of the shank 26. In this embodiment, the bore 34 begins at the distal end 30 and exits through a side 40 of the shank 26. In other words, in relation to the longitudinal axis 36 of the shank 26, the bore 34 is angularly rotated about the distal end 30 of the shank forming an acute angle α with the longitudinal axis. For the purposes of this application, the term "off-axis" shall be taken to mean a bore having a center longitudinal axis which is non-concentric in relation to the center longitudinal axis of the shank. Thus, an off-axis bore may run either laterally parallel to the longitudinal axis of the shank or be angularly rotated about the distal end of a shank as illustrated in FIG. 2.

As previously described, anchors, such as anchor 12, are typically subjected to relatively large forces. The large external forces and the overall placement of such anchors result in localized regions of higher stresses which may cause the anchor to break in such regions. A typical region of higher stress is illustrated as region 42. The region 42 is generally located along the shank 26 below the proximal end 28 of the shank 26. Note that in this embodiment, the cross sectional area of the shank 26 in region 42 has not been reduced. Thus, the full cross-sectional area of the shank 26 is available in this region to resist the applied forces. Furthermore, the use of the full cross-sectional area (without cannulation) reduces the stress in the region 42 which may greatly increase the strength of the anchor 12.

This arrangement is in contrast to conventional cannulated pedicle screws which have a cannluation extending entirely through the screw along their longitudinal center axes. The cannulation causes a reduction in cross sectional area at high stress locations which contributes to a failure of the cannulated screw.

The bore 34 may receive a guide wire (not shown). Because the bore does not cause a cannulation through the entire length of the anchor, the bore may be of a relatively larger diameter when compared to conventional cannulated pedicle screws. The larger diameter bore allows the guide wire to also have a larger diameter, which increases the strength of the guide wire and reduces wire advancement and kinking. Furthermore, the larger diameter increases the strength of the guide wire and may allow a surgeon to have tactile feedback regarding the placement and location of the guide wire.

By having the guide wire exit the side of the anchor, the surgeon can keep hold of the proximal end of the guide wire at all times throughout the procedure. This may help ensure that the guide wire does not advance as the screw is slid down the wire. Additionally, the relative short length of the bore 34 (compared to a conventional cannulated screw) will tend to reduce the friction between the instruments and the guide wire, thereby reducing guide wire advancement. Guide wire advancement will also be reduced because the guide wire is pulled out prior to advancing the anchor so there is no guide wire advancement during screw insertion as with conventional cannulated systems.

Figure 3C:
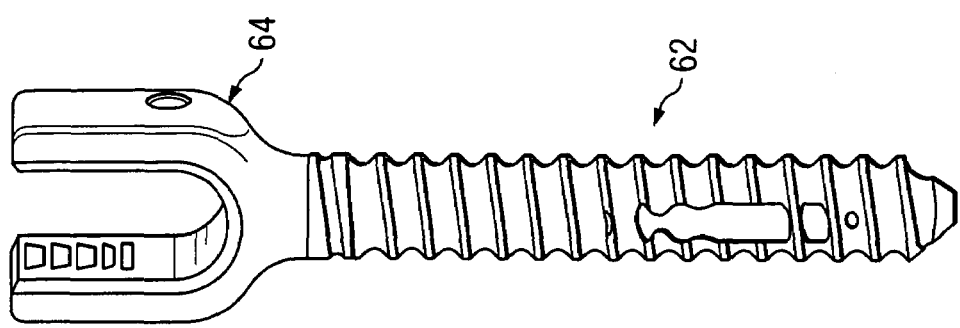
FIG. 3c illustrates a front view of yet another alternative embodiment of an anchoring device which incorporates one or more aspects of the present invention.
Figure 3B:
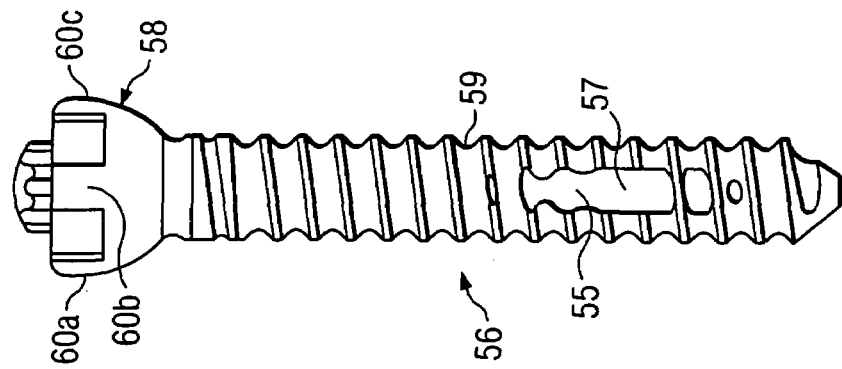
FIG. 3b illustrates a front view of an alternative embodiment of an anchoring device which incorporates one or more aspects of the present invention.
Figure 3A:
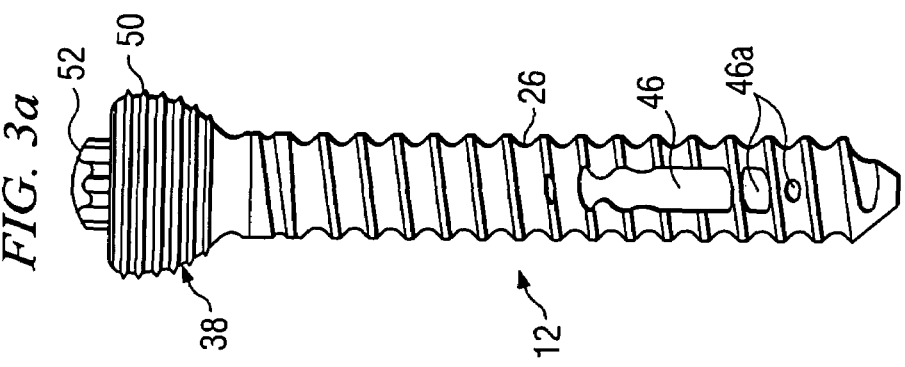
FIG. 3a illustrates a front view of an illustrative embodiment of an anchoring device which incorporates one or more aspects of the present invention.

Turning now to FIG. 3a, there is illustrated a front view of one embodiment of the anchor 12. As illustrated, the bore 34 (FIG. 2) forms a generally elongated opening 46 with the front side of the shank 26. In some embodiments, there may be a series of smaller openings 46a formed by the threads and the bore. In this illustrative embodiment, the head 38 of the anchor 12 may include an external helical thread 50. In some embodiments, the helical thread 50 may be a "reverse" screw thread which may be adapted to engage a corresponding reverse screw thread of the rod receiving part 14 (FIG. 1). For purposes of this application, a reverse screw thread is a thread designed to engage a corresponding thread in an opposite rotational direction when compared to conventional threads. The head 38 may include various recesses and/or protrusions 52 to engage a driving device (not shown) that may be used to drive the anchor 12 into the bone (not shown). In some embodiments, the driving device may also be used to remove an installed anchor from a bone.

FIG. 3b illustrates a front view of an off-axis pedicle screw 56 incorporating various aspects of the present invention. As illustrated, a bore 57 forms a generally elongated opening 55 with one side of a shank 59. The off-axis pedicle screw 56 has an alternative embodiment of a head 58. In this illustrative embodiment, the head 58 may include one or more splines, for example splines 60a, 60b, and 60c. The splines 60a, 60b, and 60c may be equally spaced circumferentially around the head 58. In some head embodiments, the splines 60a, 60b, and 60c may be spaced at unequal distances circumferentially around the head 58. The splines 60a, and 60b, and 60c may include surface protrusions, recesses and/or texturing to enhance coupling of the off-axis pedicle screw 56 with a ring of a bone fastener assembly (not shown). In some embodiments, sides of the splines 60a, 60b, and 60c may have a tapering so that the splines form a dovetail connection with a ring. In some embodiments, the spline width may be tapered so that a good interference connection is established when the bone screw is coupled to a ring. Splines 60a, 60b and 60c may include one or more projections (not shown) to facilitate coupling the head 58 to an inner surface of a ring which may be part of the rod receiving part assembly.

Turning now to FIG. 3c, there is illustrated a front view of another alternative embodiment of an off-axis pedicle screw 62. In some embodiments, the off-axis pedicle screw 62 may be a have a head 64 which is adapted to be a fixed angle fastener as depicted in FIG. 3c. Such fixed angle fastener heads are well known in the art.

FIG. 4 illustrates the anchor 12 coupled to a guide wire 72. As will be explained in detail below, once the guide wire 72 is in place, the guide wire 72 may be slipped through the bore 34 (not shown) of the anchor 12 as illustrated in FIG. 4. The anchor may also be coupled to a driving device 70.

As illustrated in FIG. 4, a distal end of driving device 70 is positioned in an external sleeve 74. In some embodiments, the sleeve 74 may be coupled to the rod receiving part 14 (FIG. 1) of the medical implant device 10. The driving device 70 may include an outer shaft 76, an inner shaft 78, and removable handle 80. The outer shaft 76 may include a textured portion 82. In some embodiments, the textured portion 82 may facilitate rotation of the outer shaft 76 without the use of the removable handle 80.

In some embodiments, the distal end of inner shaft 78 (not shown) may be coupled to the anchor 12 during use. The proximal end 81 of the inner shaft 78 may be coupled to the removable handle 80. Thus, during the anchor placement, the inner shaft 78 may be rotatable relative to outer shaft 76 so that anchor 12 can be inserted into a bone. In some embodiments, a proximal portion of the inner shaft 78 may include a coupling portion (not shown) which is adapted to mate with the removable handle 80. The removable handle 80 may also be adapted to fit other instruments which may be used in the procedure such as a bone awl and/or a bone tap (not shown).

FIG. 5 illustrates an isometric view of an illustrative embodiment of a dilator 84 which may be used with various aspects of the present invention. As will be explained below, dilators are typically used in spinal procedures. The dilator 84 has a longitudinal slot 86 which allows the guide wire 72 to extend outside of the dilator during use.

Figure 6:
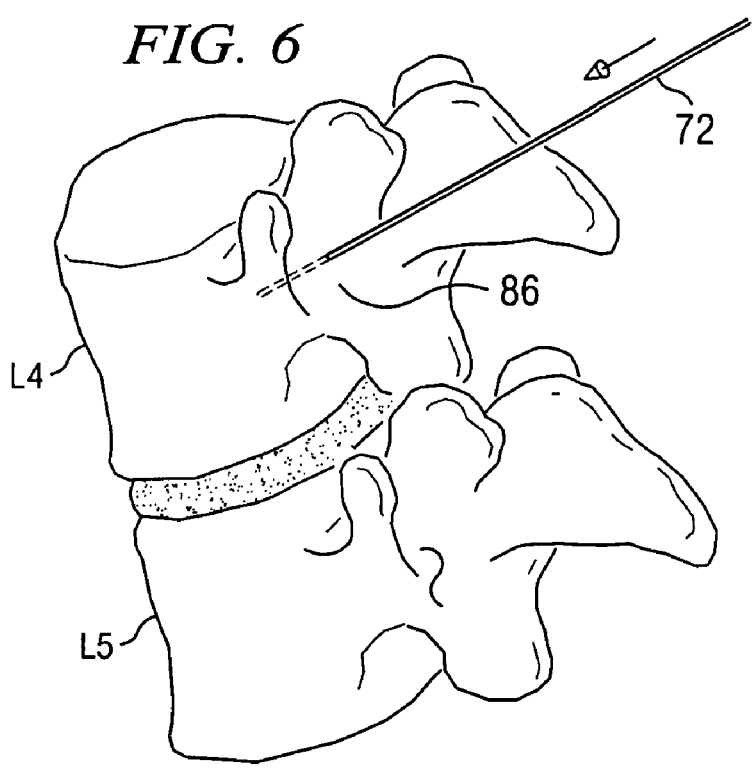
FIG. 6 illustrates one step in an illustrative embodiment of a procedure for implanting a guided anchoring device.

Referring now to FIGS. 6 to 11, the manner of using certain aspects of the present invention will now be described. The surgeon identifies the desired vertebral levels and pedicle positions via standard techniques. Once the target vertebrae are identified, a small incision is made through the skin and a tracking needle (or other device) is inserted to pinpoint exactly where each anchor is to be placed. A fluoroscope, or other x-ray technique, may be used to properly position the tracking needle. Once the proper position is located, the guide wire 72 may be positioned with its distal end against the pedicle, in this case pedicle 86 of vertebrae L4 as illustrated in FIG. 6.

Figure 7:
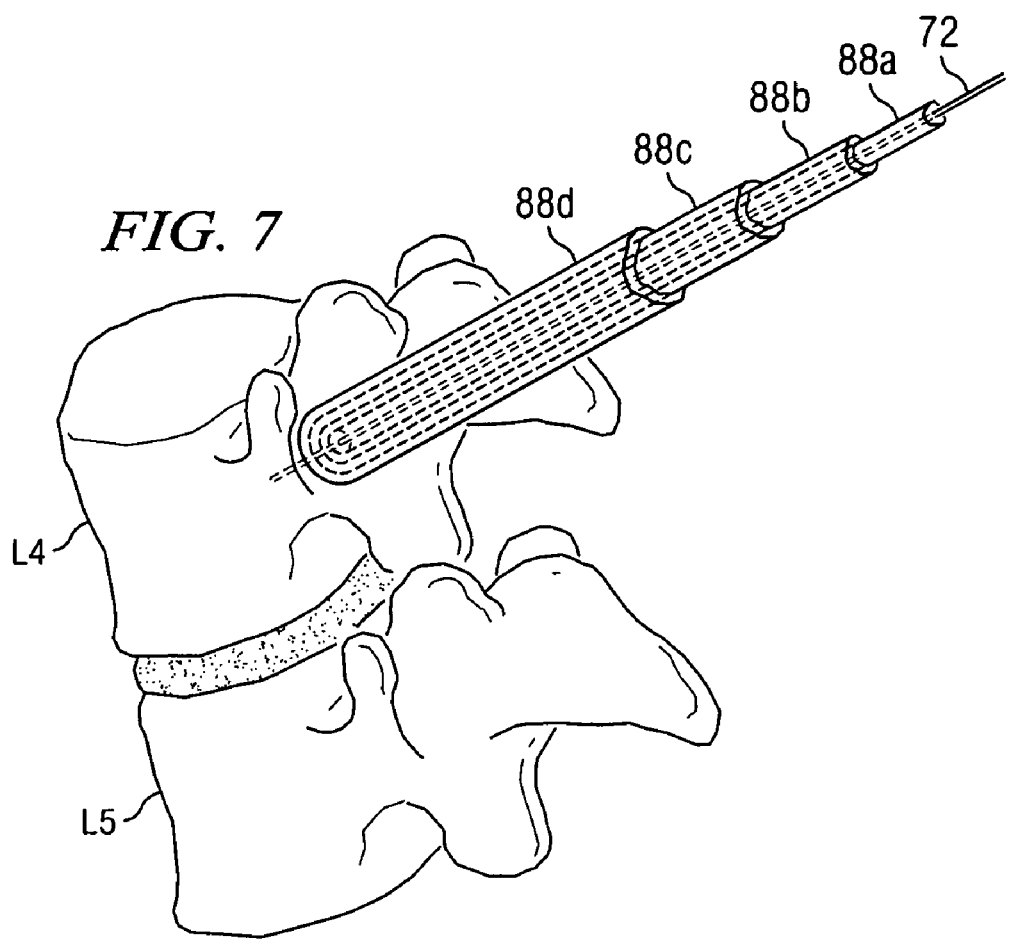
FIG. 7 illustrates one step in an illustrative embodiment of a procedure for implanting a guided anchoring device.

As shown in FIG. 7, the surgeon may then slide a series of continuing larger sized dilators 88a, 88b, 88c, and 88d down the guide wire 72. Approximately four or five dilators are used until a diameter suitable for passing the anchor and its extensions is achieved. In some embodiments, the last dilator used will be the slotted side dilator 84 discussed with reference to FIG. 5. Once slotted dilator 84 is in place, the other dilators 88a through 88d may be removed. In some embodiments, a bone awl and/or bone tap may inserted over the guide wire to tap a hole into the pedicle in preparation for receiving the anchor 12, which in this case may be a pedicle screw. This tap will usually be a size slightly smaller than the pedicle screw thread size selected for that patient and that level.

Figure 8:
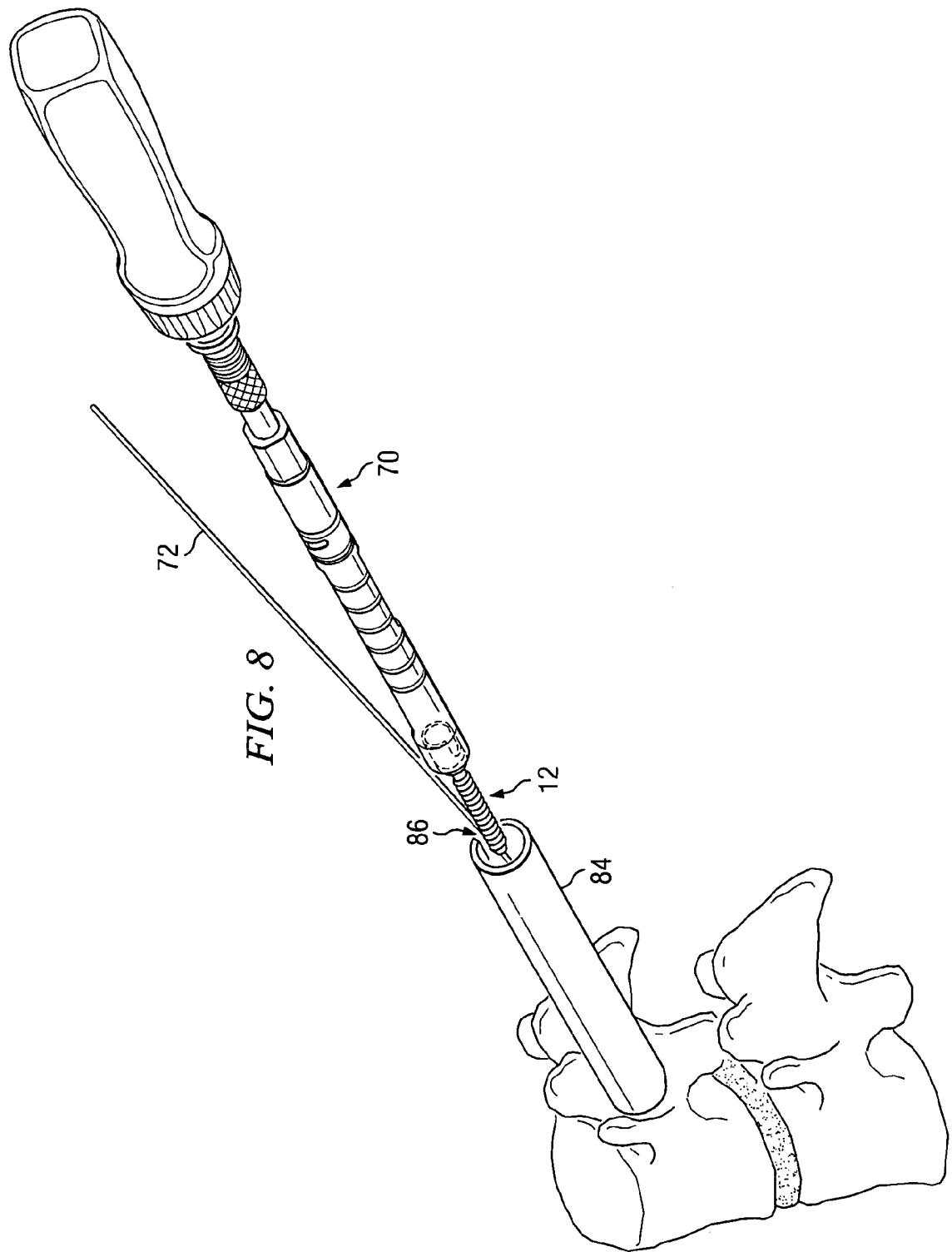
FIG. 8 illustrates one step in an illustrative embodiment of a procedure for implanting a guided anchoring device.
Figure 9:
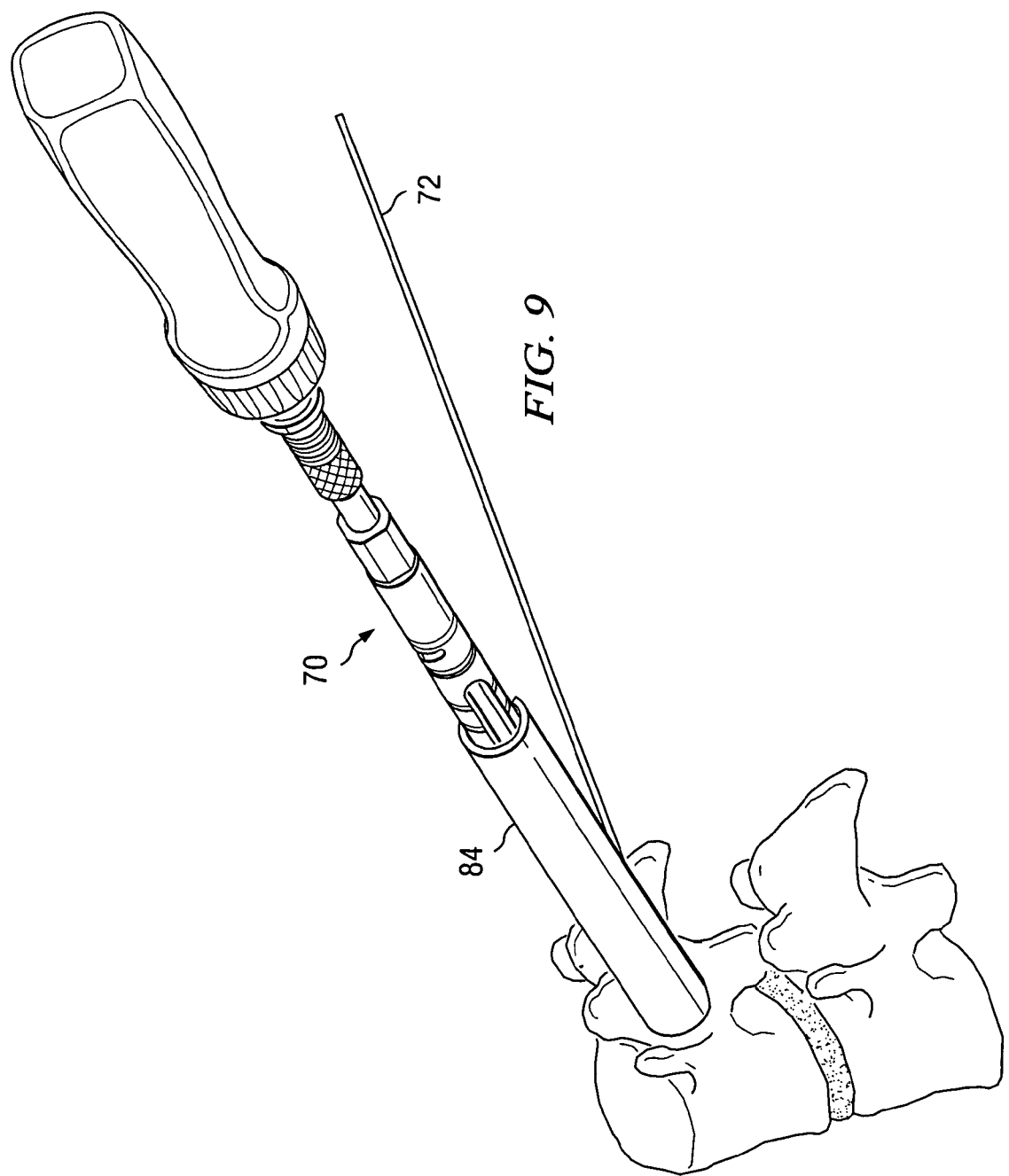
FIG. 9 illustrates one step in an illustrative embodiment of a procedure for implanting a guided anchoring device.

After the hole is tapped and the inner dilators, such as dilators 88a-88d are removed, the surgeon is ready to introduce the anchor 12 into the vertebrae. As shown in FIG. 8, prior to inserting the anchor 12 (e.g., pedicle screw), the guide wire 72 is placed through the off-axis bore 34 (not shown) of the anchor 12. The anchor 12 may be coupled to the driving device 70 as previously described. The driving device 70 engages the proximal end of the anchor 12. As the anchor 12 and the distal end of the driving device 70 enters the slotted dilator 84, the slot 86 of the dilator allows the guide wire 72 to extend beyond the passage of the dilator 84 as illustrated in FIG. 9.

Figure 10:
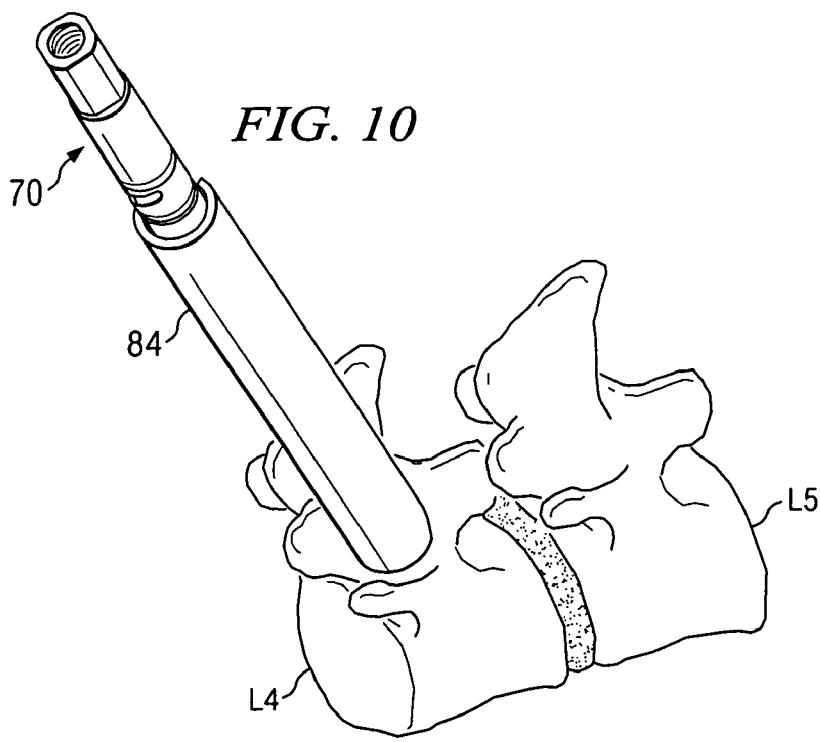
FIG. 10 illustrates one step in an illustrative embodiment of a procedure for implanting a guided anchoring device.
Figure 11:
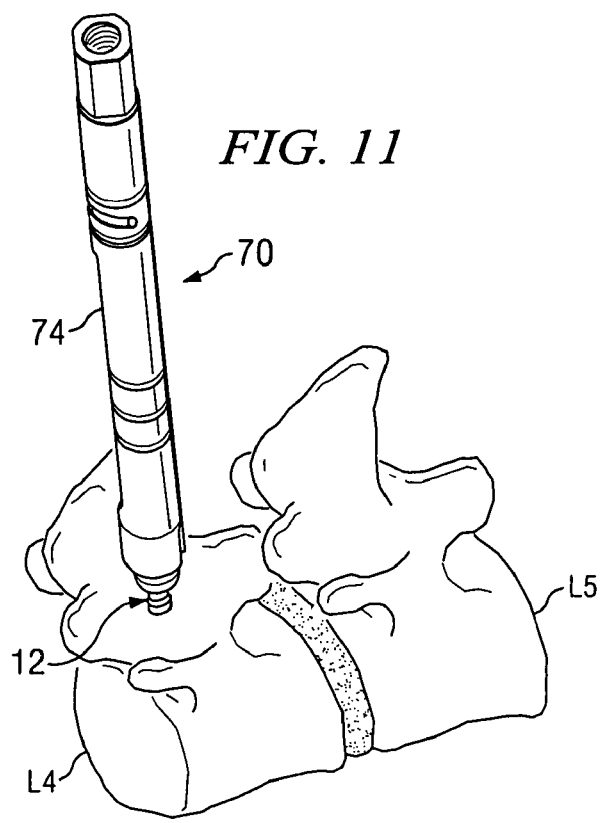
FIG. 11 illustrates one step in an illustrative embodiment of a procedure for implanting a guided anchoring device.

Once the anchor 12 is in position, which may be verified by flourscopy techniques, the guide wire 72 may be removed. It may also be desirable at this stage to also remove the dilator 84. To accomplish this, the removable handle 80 may be removed in order to allow the dilator 84 to slip over the driving device 70 as shown in FIG. 10. Once the anchor 12 is in position, the driving device 70 may then be rotated into a proper position, as shown in FIG. 11. The surgeon may then screw the anchor 12 into the pre-tapped hole in vertebrae L4. Pressure on the driving device 70 forces the anchor to be in-line with the external sleeve 74. A similar procedure may be repeated for each additional level, in this case level L5.

Figure 12:
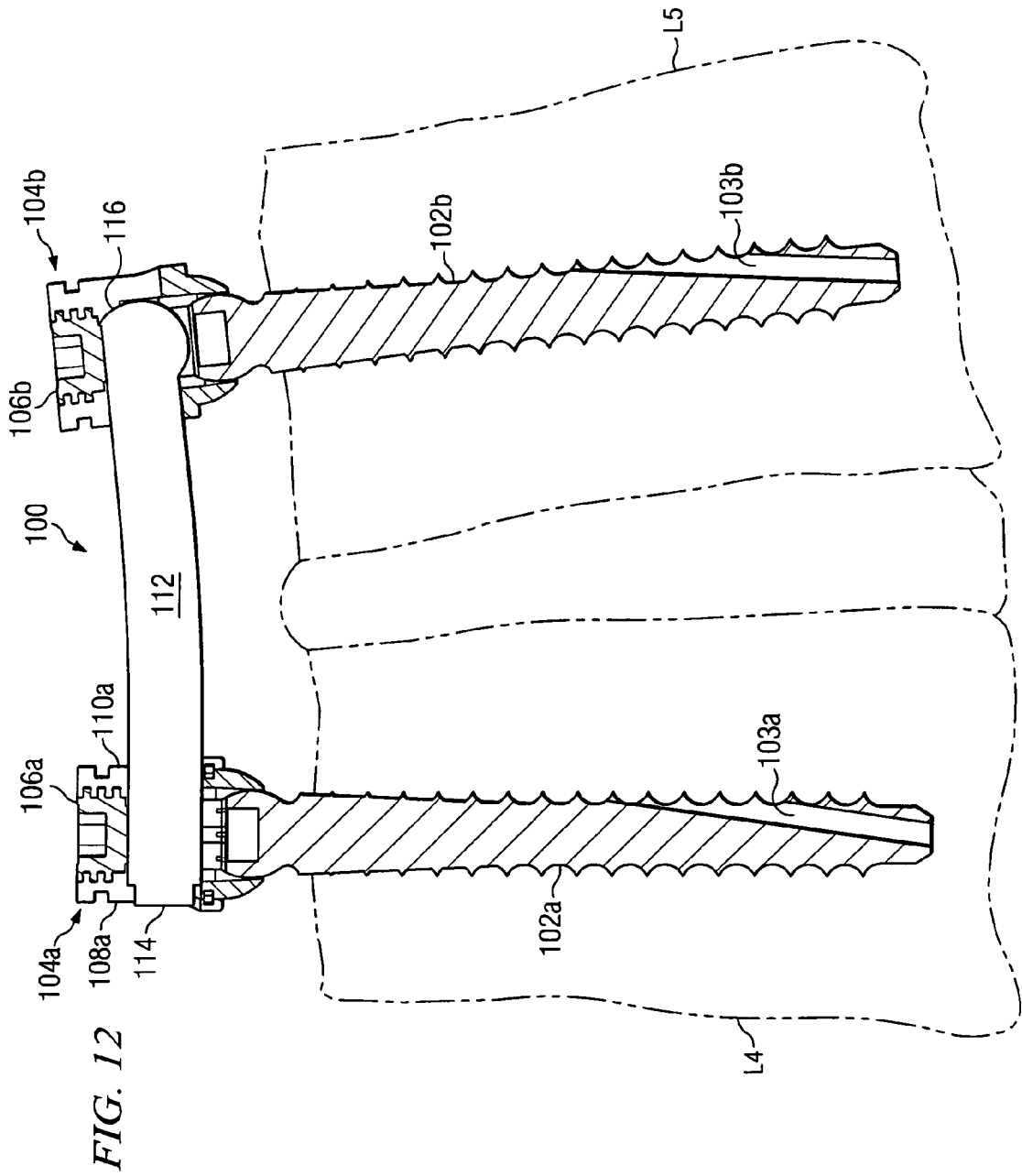
FIG. 12 illustrates an example stabilization device configuration which may result from the procedure described in reference to FIGS. 6 to 11.

Once the pedicle screws are in place, an assembly may be coupled to the pedicle screws. For instance, FIG. 12 shows an example medical implant device 100. A similar medical implant device 100 is described further in co-pending and commonly assigned U.S. patent application Ser. No. 10/690,211 filed Oct. 21, 2003 titled "SYSTEM AND METHOD FOR STABILIZATION OF INTERNAL STRUCTURES" (hereafter "the '211 patent application), the disclosure of which is hereby incorporated herein by reference. More specifically, medical implant device 100 may be a stabilization device that may include pedicle screws (or "anchors") 102a and 102b that are inserted into vertebrae of a patient's spine, such as vertebrae L4 and L5, respectively. The pedicle screws have off-axis bores 103a and 103b which have been used in conjunction with guide wires (not shown) to guide the screws to the proper location. Assemblies 104a and 104b may be coupled to pedicle screws 102b and 102a, respectively. Such assemblies 104a and 104b each form a receiving member for receiving closure member (e.g., set screw 106a or 106b). Generally, such receiving member formed by assemblies 104a and 104b is a noncontiguous (e.g., open-back member) having at least two walls, such as walls 108a and 110a, that are separated by slots.

In this illustrative embodiment, closure member 106a and walls 108a and 110a are formed to have complementary threads that are formed in a manner that aids in preventing splaying of the receiving members. In the specific implementation shown, closure member 106 and walls 108a and 110a of the receiving member are dovetail configurations, such as described in the '967 patent application. Of course, other interlocking configurations, may be used in alternative implementations. As further shown in FIG. 12, a brace (or "rod") 112 extends from assembly 104a to assembly 104b, and closure members (e.g., set screws) 106 are used for securing a first end 114 of the brace 112 to the pedicle screw 102a and the other end 116 of the brace 112 to pedicle screw 102b.

Thus, the medical implant device 100 may be installed using various aspects of the present invention. As previously described, the anchors 102a and 102b are able to resist larger forces than conventional cannulated screws. Furthermore, because the bores 103a and 103b do not cause a cannulation through the entire length of the anchors, the bores may be of a relatively larger diameter when compared to conventional cannulated pedicle screws. The larger diameter bore allows the guide wire to also have a larger diameter, which increases the strength of the guide wire, reduces kinking, allows a surgeon to have tactile feedback regarding the placement and location of the guide wire, and allows the surgeon can keep hold of the proximal end of the guide wire at all times throughout the procedure. The relative short length of the bore reduces the friction between the instruments and the guide wire, thereby reducing guide wire advancement.

It is important to note that any such advantages and benefits described in this application may not apply to all embodiments of the invention. When the word "means" is recited in a claim element, Applicant intends for the claim element to fall under 35 USC 112, paragraph 6. Often a label of one or more words precedes the word "means". The word or words preceding the word "means" is a label intended to ease referencing of claims elements and is not intended to convey a structural limitation. Such means-plus-function claims are intended to cover not only the structures described herein for performing the function and their structural equivalents, but also equivalent structures. For example, although a nail and a screw have different structures, they are equivalent structures since they both perform the function of fastening. Claims that do not use the word means are not intended to fall under 35 USC 112, paragraph 6.

The foregoing description of the embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims. For instance, various embodiments of the present invention could be integrated into various navigational systems, such as the GE EM Tracking system.

The abstract of the disclosure is provided for the sole reason of complying with the rules requiring an abstract, which will allow a searcher to quickly ascertain the subject matter of the technical disclosure of any patent issued from this disclosure. It is submitted with the understanding that it will not be used to interpret or limit the scope or meaning of the claims.

What is claimed is:

1. A system for guiding bone anchors, the system comprising:
   a guide wire
   an anchor comprising:
      a shank having a proximal end and a distal tip, wherein the shank has an offset bore which is adapted to allow the guide wire to slide through the bore, wherein the bore extends from the distal tip of the shank to a side surface of the shank, and wherein the shank does not have a bore which causes a cannulation through the entire length of the anchor; and
      a head coupled to a proximal end of the shank;
   a dilator having a longitudinal slot where the longitudinal slot allows the guide wire to extend through the longitudinal slot when the anchor is positioned within the dilator; and
   a driving device which is adapted to engage the head of the anchor.

2. The system of claim 1 wherein the bore is not concentric to a longitudinal center axis of the shank.

3. The system of claim 1 wherein the driving device further comprises:
   an outer shaft,
   an inner shaft rotatably disposed within the outer shaft having a distal end and a proximal end, and
   a removable handle coupled to the proximal end.

4. The system of claim 3 wherein the outer shaft is adapted to couple with a rod receiving portion of a medical implant device and the distal end of the inner shaft is adapted to engage the anchor.

* * * * *